United States Patent
Karunasiri et al.

(10) Patent No.: US 12,372,415 B2
(45) Date of Patent: Jul. 29, 2025

(54) TEMPERATURE SENSING ARCHITECTURES FOR IMPLANTABLE DEVICE

(71) Applicant: Advanced Bionics AG, Staefa (CH)

(72) Inventors: R. Tissa Karunasiri, Valencia, CA (US); Scott Kenneth Arfin, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 763 days.

(21) Appl. No.: 17/619,477

(22) PCT Filed: Jun. 28, 2019

(86) PCT No.: PCT/US2019/039924
§ 371 (c)(1),
(2) Date: Dec. 15, 2021

(87) PCT Pub. No.: WO2020/263280
PCT Pub. Date: Dec. 30, 2020

(65) Prior Publication Data
US 2022/0307912 A1    Sep. 29, 2022

(51) Int. Cl.
*A61B 5/01*   (2006.01)
*A61B 5/00*   (2006.01)
(Continued)

(52) U.S. Cl.
CPC .............. *G01K 7/015* (2013.01); *A61B 5/01* (2013.01); *A61B 5/686* (2013.01); *A61N 1/08* (2013.01);
(Continued)

(58) Field of Classification Search
CPC .. A61B 5/01; A61B 5/686; A61N 1/08; A61N 1/36038; G01K 13/20
See application file for complete search history.

(56) References Cited

U.S. PATENT DOCUMENTS 6,157,244 A    12/2000 Lee et al.
6,501,256 B1   12/2002 Jaussi et al.
(Continued)

FOREIGN PATENT DOCUMENTS

| WO | 2006003074 | 1/2006 |
| WO | 2009055865 | 5/2009 |
| WO | 2009055866 | 5/2009 |

OTHER PUBLICATIONS

"International Search Report and Written Opinion received in International Application No. PCT/US19/39924."
(Continued)

*Primary Examiner* — Joseph M Dietrich
(74) *Attorney, Agent, or Firm* — ALG Intellectual Property, LLC

(57) ABSTRACT

A system may include a device configured to be implanted within a recipient and that includes an integrated circuit. The integrated circuit may include a first node configured to provide a bandgap reference voltage and a second node configured to provide a CTAT voltage. The first node may be coupled to a first input of an ADC and the second node may be coupled to a second input of the ADC. The system may also include a processor communicatively coupled to an output of the ADC. The processor may be configured to determine, based on the output of the ADC, the CTAT voltage. The processor may be further configured to determine, based on the CTAT voltage, a temperature of the device.

14 Claims, 6 Drawing Sheets

(51) Int. Cl.
  *A61N 1/08* (2006.01)
  *A61N 1/36* (2006.01)
  *G01K 7/01* (2006.01)
  *G01K 13/20* (2021.01)

(52) U.S. Cl.
  CPC ......... *A61N 1/36038* (2017.08); *G01K 13/20* (2021.01); *G01K 2219/00* (2013.01)

(56) References Cited

U.S. PATENT DOCUMENTS

| | | |
|---|---|---|
| 6,605,987 B2 | 8/2003 | Eberlein |
| 7,037,273 B2 | 5/2006 | Zhu et al. |
| 7,313,044 B2 | 12/2007 | Fuhrmann et al. |
| 8,632,463 B2 | 1/2014 | Drinan et al. |
| 9,060,692 B2 | 6/2015 | Pertijs |
| 2008/0262331 A1 | 10/2008 | Gerber et al. |
| 2010/0124251 A1 | 5/2010 | Peterson |
| 2011/0035231 A1 | 2/2011 | Firminger et al. |
| 2011/0106101 A1 | 5/2011 | Tortonese et al. |
| 2011/0255568 A1 | 10/2011 | Swe |
| 2013/0136149 A1 | 5/2013 | Soenen et al. |
| 2013/0261497 A1* | 10/2013 | Pertijs ................. A61B 5/6876 600/549 |
| 2013/0343585 A1 | 12/2013 | Bennett et al. |
| 2015/0238354 A1 | 8/2015 | Rajguru et al. |
| 2016/0310077 A1 | 10/2016 | Hunter et al. |
| 2017/0042713 A1 | 2/2017 | Nurmikko et al. |
| 2019/0199329 A1 | 6/2019 | Shor |

OTHER PUBLICATIONS

Banba, et al.,"A CMOS Bandgap Reference Circuit with Sub-1-V Operation", IEEE Journal of Solid-State Circuits, vol. 34, No. 5, May 1999, pp. 670-674.

Long, et al.,"Using Temperature to Analyze Temporal Dynamics in the Songbird Motor Pathway", Nature 456.7219 (2008): 189-194.

* cited by examiner

TEMPERATURE SENSING ARCHITECTURES FOR IMPLANTABLE DEVICE

BACKGROUND INFORMATION

Cochlear implants and other implantable medical devices are implanted in recipients to provide benefits for medical purposes. For example, cochlear implants may improve or enable hearing in a recipient lacking full hearing capabilities. Other implantable medical devices may help or enable diagnosis, treatment, monitoring, preventing, etc. of medical conditions. The operation of some implantable medical devices may be affected by temperature. Thus, it may be helpful to include a temperature sensor on the device. However, adding a component such as a temperature sensor may increase complexity, cost, resource usage, and/or have other disadvantages.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Temperature sensing architectures for an implantable device are described herein. To illustrate, a system may include a device (i.e., an implantable device) configured to be implanted within a recipient and that includes an integrated circuit. The integrated circuit includes a first node configured to provide a bandgap reference voltage and a second node configured to provide a complementary to absolute temperature (CTAT) voltage. The first node is coupled to a first input of an analog-to-digital converter (ADC) and the second node is coupled to a second input of the ADC. The system may also include a processor communicatively coupled to an output of the ADC. The processor is configured to determine, based on the output of the ADC, the CTAT voltage. The processor may be further configured to determine, based on the CTAT voltage, a temperature of the device.

The architectures, systems, and methods described herein may leverage circuitry already included in some implantable devices to facilitate temperature monitoring of the implantable devices. For example, an implantable device (e.g., a cochlear implant or a neurostimulator) may include a bandgap circuit configured to receive a high voltage supply (e.g., greater than 10 volts (V)) provided by radio frequency (RF) telemetry and, based on the high voltage, output a temperature invariant bandgap reference voltage used to provide a low voltage analog power supply (e.g., less than 5 V) for components within the implantable device that require and/or run more efficiently at lower voltages. The architectures, systems, and methods described herein may utilize the bandgap circuit to also determine a temperature of the implantable device. In this manner, the circuitry of the implantable device may not have to be extensively modified and/or added to in order to provide temperature monitoring functionality.

The architectures, systems, and methods described herein may also advantageously facilitate monitoring of a body temperature of a recipient of an implantable device. For example, as described herein, a processor may determine body temperature based on device temperature. This may allow dynamic and automatic optimization of implantable device function (e.g., by adjusting one or more parameters that control stimulation applied by a cochlear implant or other type of neurostimulator to optimize the stimulation for a particular body temperature). Moreover, the processor may be further configured to notify the recipient of a change in the recipient's body temperature, which may be advantageous for a variety of reasons. These and other advantages and benefits of the present architectures, systems, and methods are described in more detail herein.

Various embodiments of temperature sensing architectures in implantable devices will now be described with reference to the figures.

Figure 1:
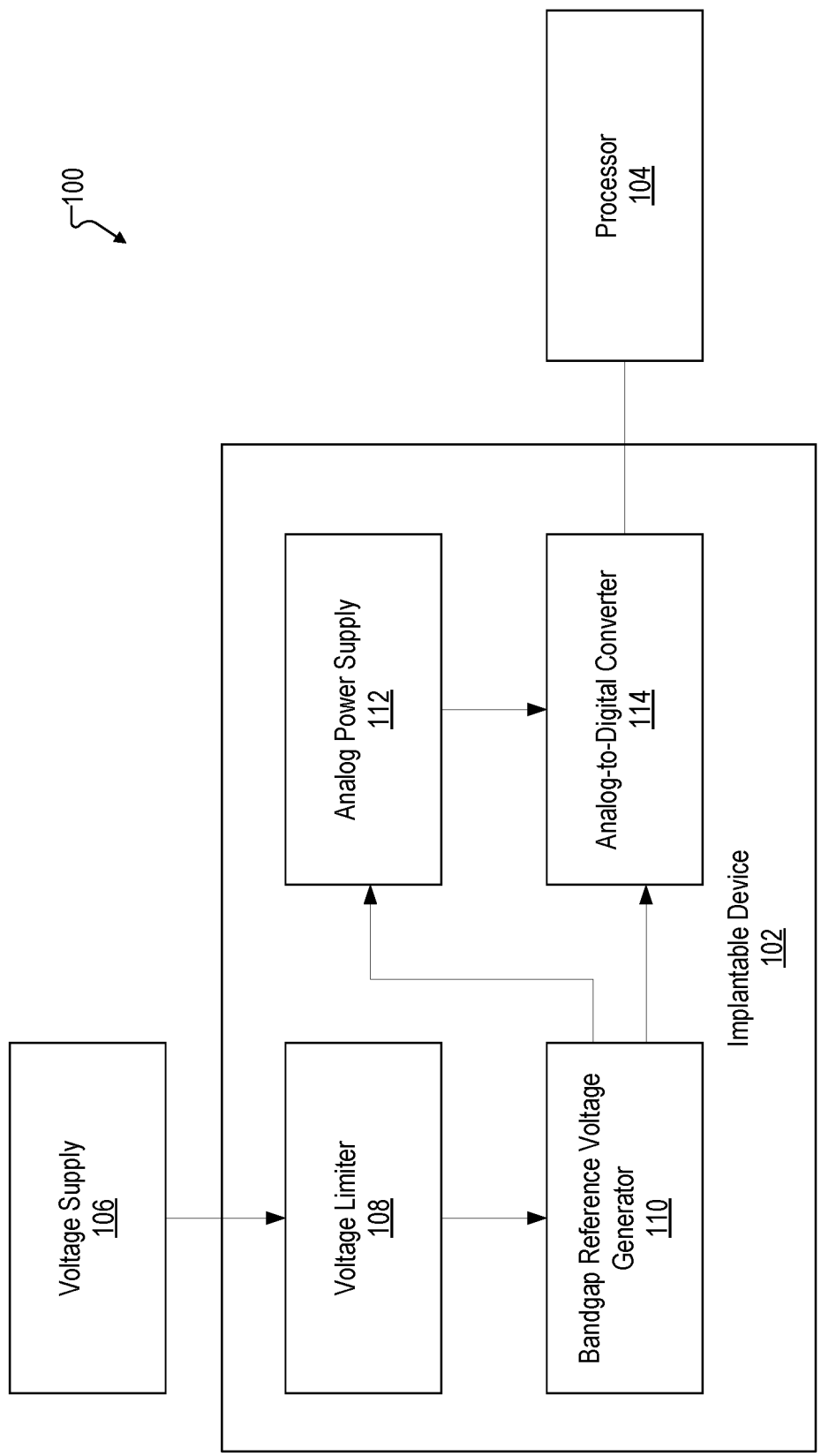
FIG. 1 illustrates an exemplary system according to principles described herein.

FIG. 1 illustrates an exemplary system 100 with a temperature sensing architecture. System 100 includes an implantable device 102, a processor 104, and a voltage supply 106. System 100 may include additional or alternative components as may serve a particular implementation.

Implantable device 102 may be implemented by any suitable implantable medical device that is configured to be implanted in a recipient. For example, implantable device 102 may be implemented by a cochlear implant, a neurostimulator, a middle ear implant, a cardiac pacemaker, an implantable drug pump, and/or any other type of implantable medical device as may serve a particular implementation.

Voltage supply 106 may be implemented in any suitable manner. For example, voltage supply 106 may be a power supply provided by circuitry external to implantable device 102 in the form of an RF signal that is wirelessly transmitted (e.g., transcutaneously) to implantable device 102. Additionally or alternatively, voltage supply 106 may be implemented by a battery or other power source included within implantable device 102. In some instances, voltage supply 106 may be a high-voltage power supply, which may be used for powering components within implantable device 102 that use high voltages (e.g., voltages greater than 10 V). Other functions of implantable device 102 may run more efficiently at lower voltages, which may be provided by other components of implantable device 102 described herein.

Processor 104 is communicatively coupled to implantable device 102 (e.g., to circuitry within implantable device 102) and may be implemented in any suitable manner. As shown, processor 104 may be external to implantable device 102 (e.g., external to the recipient). For example, as described herein, processor 104 may be implemented by a sound processor configured to control a cochlear implant and be located external to a recipient of the cochlear implant. In other examples, processor 104 may be included within implantable device 102.

In the example of FIG. 1, implantable device 102 includes a voltage limiter 108, a bandgap reference voltage generator 110, an analog power supply 112, and an analog-to-digital converter (ADC) 114. Some or all of voltage limiter 108, bandgap reference voltage generator 110, analog power supply 112, and ADC 114 may be implemented on one or more integrated circuits on implantable device 102.

As shown, voltage limiter 108 is connected to voltage supply 106. In this configuration, voltage limiter 108 limits the high voltage provided by voltage supply 106 in a manner that provides protection to bandgap reference voltage generator 110 and other components of implantable device 102. Voltage limiter 108 may be implemented in any suitable manner. In some alternative examples, voltage limiter 108 may not be included in implantable device 102. In these alternative examples, voltage supply 106 may be connected directly to bandgap reference voltage generator 110.

Bandgap reference voltage generator 110 is configured to generate, based on the voltage supplied by voltage supply 106 and limited by voltage limiter 108, a bandgap reference voltage. The bandgap reference voltage may be configured to be a voltage that is invariant with respect to changes in temperature.

Bandgap reference voltage generator 110 may be implemented in any suitable manner. As an example, bandgap reference voltage generator 110 may generate the bandgap voltage by generating and combining a proportional to absolute temperature (PTAT) voltage and a CTAT voltage. As the PTAT voltage varies proportionally with the absolute temperature and the CTAT voltage varies in a complementary manner with the absolute temperature, combining the PTAT and CTAT voltages may provide an output voltage that is invariant with temperature and that may be used as a reference voltage. Implantable device 102 may use the bandgap reference voltage for various functions, such as providing a baseline for which to measure other voltages. For example, for a cochlear implant system, the bandgap reference voltage may be used to measure suitable voltages to be provided for electrical stimulation to improve and/or enable hearing. The bandgap reference voltage may also be provided to analog power supply 112 to generate a stable power output. The bandgap reference voltage may be any suitable voltage (e.g., 0.5 V, 1 V, 2 V, etc.). In one example implementation, bandgap reference voltage generator 110 may provide a bandgap reference voltage of 0.6 V.

Analog power supply 112 may be implemented in any suitable manner, such as a low-dropout (LDO) regulator. Analog power supply 112 may receive the bandgap reference voltage from bandgap reference voltage generator 110 and generate an output power supply voltage. The power supply voltage may be any suitable voltage. For example, analog power supply 112 may receive a bandgap reference voltage of 0.6 V and generate an output voltage of 4 V. In some alternative examples, analog power supply 112 may not be included in implantable device 102. In these alternative examples, bandgap reference voltage generator 110 may be connected directly to ADC 114.

ADC 114 may be implemented in any suitable manner. ADC 114 may receive the output voltage from analog power supply 112. The output voltage received from analog power supply 112 may determine a scale with which ADC 114 may output voltage differences. For example, ADC 114 may receive a 4 V output voltage from analog power supply 112. Further, ADC 114 may be implemented with a 12-bit digital output. With a 12-bit ADC and a 4 V input range, ADC 114 may provide outputs that are quantized at 1 mV. Other suitable input voltages and ADC bit sizes may be used to provide a desired sensitivity to voltage changes.

ADC 114 may also receive the CTAT voltage from bandgap reference voltage generator 110. Based on the CTAT voltage and the input voltage, ADC 114 may provide an output that correlates to changes in the CTAT voltage. ADC 114 may provide the output to processor 104.

Processor 104 may receive the output from ADC 114 and determine the CTAT voltage. As the CTAT voltage changes proportionally to temperature, processor 104 may then determine a temperature of implantable device 102 based on the CTAT voltage. For example, the CTAT voltage may decrease by approximately 2 mV for every 1 degree Celsius (° C.) increase. With this example ratio, using the example 12-bit ADC with 4 V input, processor 104 may be configured to determine temperature changes in implantable device 102 with a 0.5° C. granularity.

In some example implementations, implantable device 102 may not include ADC 114. In such implementations, a differential amplifier or any other suitable component or components may be used to determine a difference between the CTAT voltage and the bandgap reference voltage. Based on the difference between the CTAT voltage and the bandgap reference voltage and based on a known temperature response of the CTAT voltage processor 104 may determine a temperature of implantable device 102.

Figure 2:
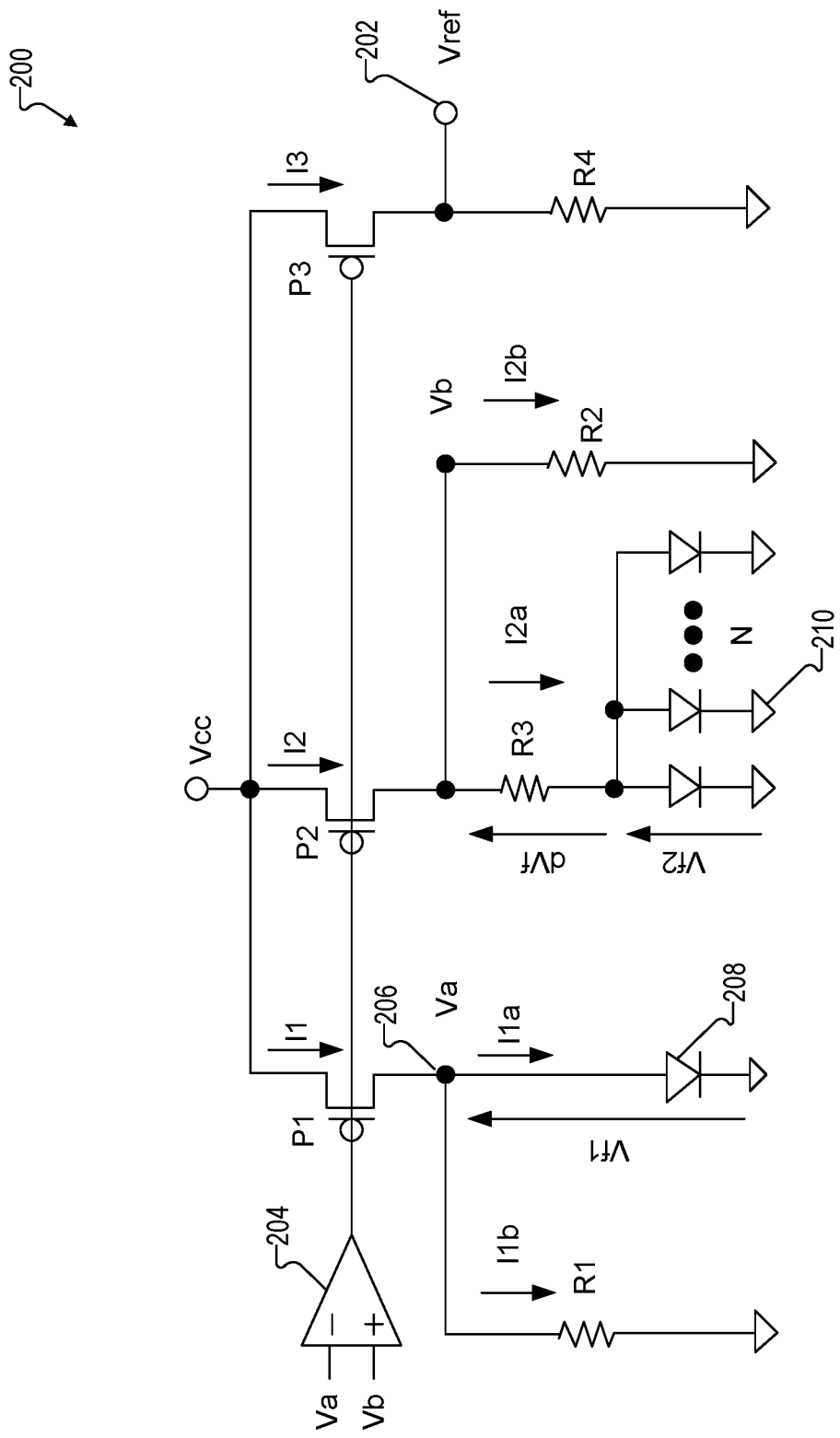
FIG. 2 illustrates an exemplary circuit of a device according to principles described herein.

FIG. 2 illustrates an exemplary circuit 200 of a temperature sensing implantable device. Circuit 200 may be an implementation of bandgap reference voltage generator 110. Circuit 200 may be implemented in any suitable manner, such as an integrated circuit on implantable device 102.

As shown, circuit 200 includes an output node 202 providing an output voltage Vref. Circuit 200 is configured such that Vref is a bandgap reference voltage, which is a stable, temperature-invariant voltage. Vref is generated based on a PTAT voltage and a CTAT voltage. Circuit 200 includes an op-amp 204 with voltages Va and Vb that are equalized. As configured, a second node 206 also provides voltage Va, which corresponds to the CTAT voltage, as described herein. Output node 202 may be coupled to a first input of an ADC (e.g., ADC 114) and second node 206 may be coupled to a second input of the ADC (e.g., by way of analog power supply 112). The ADC may use these inputs to generate an output that is provided to a processor to determine a temperature of the device, as described herein.

Circuit 200 is also configured with a current mirror such that three currents, I1, I2, and I3 are equalized. Circuit 200 also includes two resistors, R1 and R2, that have an equal resistance. As a result, two currents, I1b and I2b, flowing through R1 and R2, respectively, are also equal. Branched currents I1a and I2a are therefore also equal. As current I1a flows through a single diode 208 while current I2a flows through an N-diode branch 210, resulting voltage Vf1 is greater than Vf2. The difference in voltages between voltages Vf1 and Vf2 is dVf, made up across a resistor R3. Voltage dVf ends up tracking thermal voltage, with a positive coefficient. Thus, for the I2 branch, (Vb/R2) equals (Vf1/R2), which is the CTAT current, plus dVf/R3, which is the PTAT current. With an appropriate value of resistance for R3, the temperature curves and sum of PTAT and CTAT currents can be flattened out. The sum current is mirrored to the output node 202 to provide the bandgap reference voltage Vref.

Figure 3:
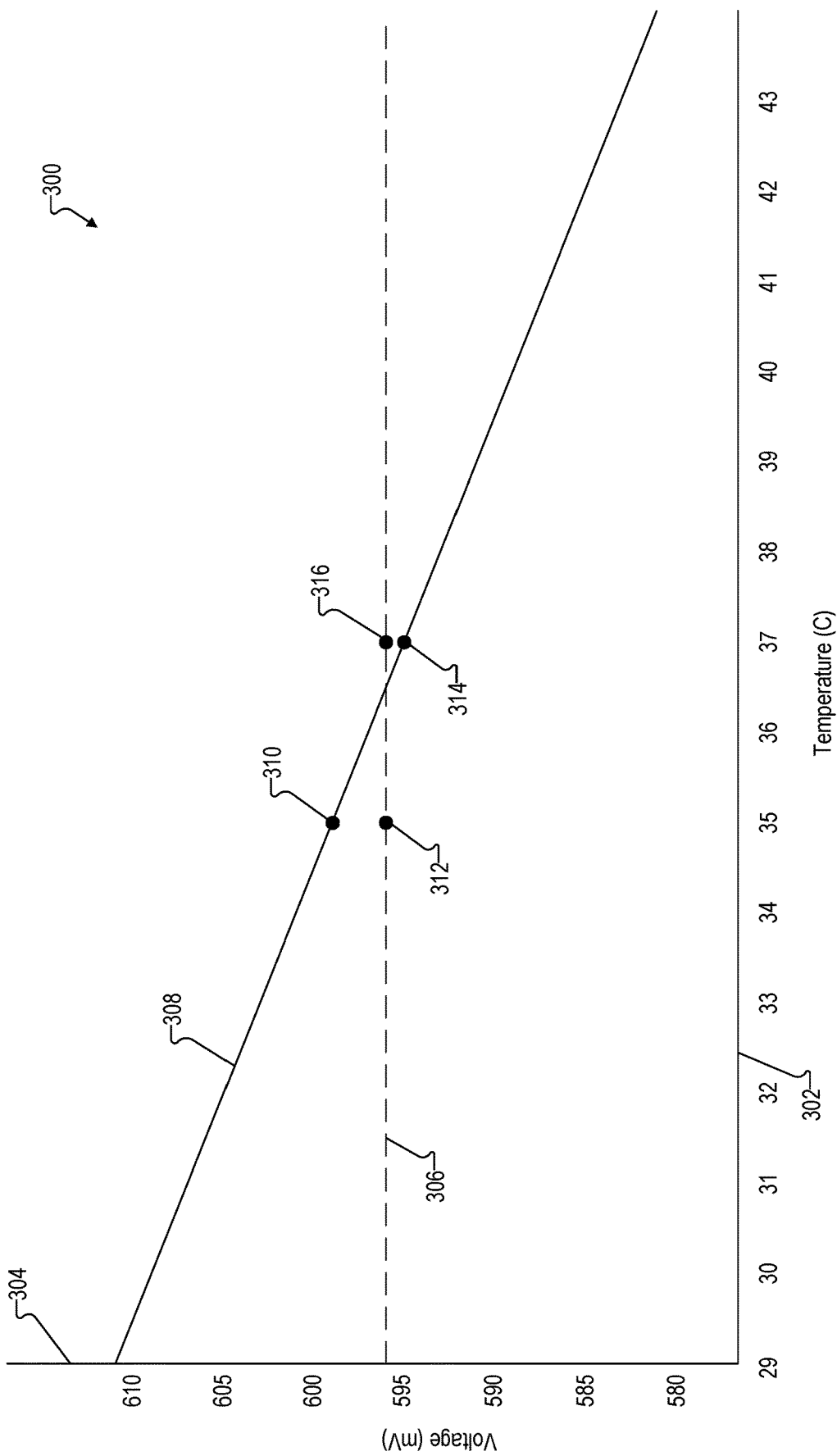
FIG. 3 illustrates a graph of an exemplary temperature response of a circuit according to principles described herein.

FIG. 3 illustrates a graph 300 of an exemplary temperature response of a circuit of a temperature sensing device, such as bandgap reference voltage generator 110 of implantable device 102. Graph 300 shows outputs of the circuit in millivolts on a y-axis 304 with respect to temperature in Celsius on an x-axis 302.

A dashed line 306 shows an example output of a bandgap reference voltage. As dashed line 306 illustrates, the bandgap reference voltage is constant across a range of temperatures. In this example, the bandgap reference voltage is shown to be approximately 596 millivolts across temperatures ranging from 29° C. to approximately 44° C.

A solid line 308 shows an example output of a CTAT voltage. As described, the CTAT voltage is negatively proportional to increasing temperature. In this example, the CTAT voltage is shown to have a slope of approximately −2 mV/° C. Thus, for every degree increase in temperature of the device, the CTAT voltage decreases approximately two millivolts. While graph 300 shows a range of temperatures from 29° C. to approximately 44° C., the CTAT voltage may demonstrate similar properties across a wider range of temperatures, which may include any practical temperatures to be encountered while implanted in a recipient and/or during manufacturing and/or initial testing.

Given the information represented on graph 300, as a processor (e.g., processor 104) receives an output from an ADC (e.g., ADC 114) coupled to the circuit, the processor may determine the value of the CTAT voltage and thereby determine the temperature of the circuit. The temperature of the circuit may correspond directly to the temperature of the device, provided that the device is not generating heat. However, the device may include components that do generate heat or receive heat (e.g., during wireless power transfer) during operation. In some examples, the device may be designed in such a way that such heat-generating and/or heat-receiving components may be isolated from the temperature sensing circuit. For instance, such components may be housed separately in the device from the temperature sensing circuit. Additionally or alternatively, the components on the device may be designed to consume low quantities of power such that any heat generated or received by components may be negligible. Further, the processor may be aware of when such components are generating or receiving heat or potentially generating or receiving heat, and take such factors into consideration. For example, the processor may not determine the temperature of the device during such operations such as power transfer or power consumption by the device above a certain threshold. Additionally or alternatively, the processor may wait a certain amount of time to ensure such heating has dissipated before determining the temperature of the device. Additionally or alternatively, the processor may determine, measure, or model an amount of heat that would be generated or received during operation of such components and take the amounts into consideration in determining the temperature of the device.

While graph 300 shows an example circuit with a slope of −2 mV/° C. and a y-intercept representing 611 mV at 29° C., other example circuits may exhibit different specific properties. For example, while CTAT voltages across different circuits may generally have an approximately similar negative proportional response (e.g., approximately −2 mV/° C.), individual circuits may have different y-intercepts, and consequently different specific values of mV output at each degree Celsius. Further, while the bandgap reference voltage across different circuits is substantially invariant with respect to temperature, the specific voltage value may differ between individual circuits. As a result, each circuit may be calibrated to determine the specific values for each device. Such a calibration may be done in any suitable manner. For example, the circuit may be heated to one or more known temperatures and the CTAT voltage and the bandgap reference voltage may be measured at the known temperatures.

Graph 300 shows an example calibration process result. Point 310 and point 312 show measurements of the CTAT voltage and the bandgap reference voltage, respectively, at 35° C. Point 310 shows the CTAT voltage is approximately 599 mV at 35° C. Point 312 shows the bandgap reference voltage is approximately 596 mV at 35° C. Point 314 and point 316 show measurements of the CTAT voltage and the bandgap reference voltage, respectively, at 37° C. Point 314 shows the CTAT voltage is approximately 595 mV at 37° C. and point 316 shows the bandgap reference voltage remains approximately 596 mV at 37° C. Using two points on each voltage line, the specific voltage values for the circuit may be determined for the remainder of the temperature values.

Figure 4:
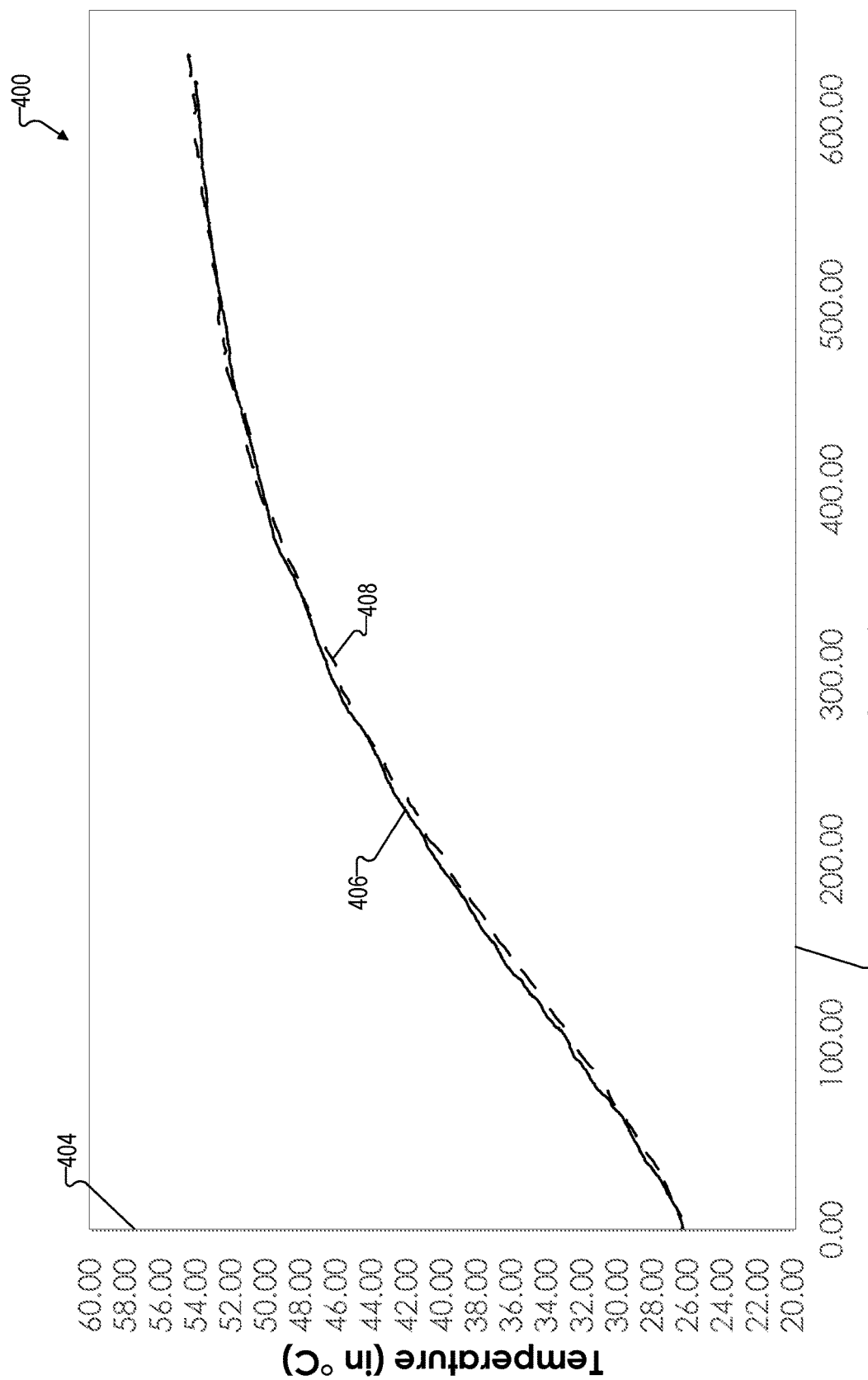
FIG. 4 illustrates a graph of an exemplary temperature response of a device according to principles described herein.

FIG. 4 illustrates a graph 400 of an exemplary temperature response of a device with a temperature-sensing architecture, such as implantable device 102. Graph 400 shows a temperature of a recipient model and a temperature of a device implanted in the recipient model as temperature (shown on a y-axis 404 in degrees Celsius) is increased over time (shown on an x-axis 402 in seconds).

Graph 400 represents an output of a simulated setup of the device implanted in a recipient model. The recipient model was heated to simulate a rise in a recipient's temperature. A solid line 406 shows the measured temperature of the recipient model as the recipient model was heated. As shown, the recipient model was heated from a temperature of approximately 26° C. to a temperature of approximately 54° C. over a time of approximately 600 seconds.

A dashed line 408 shows the temperature of the device as determined based on a CTAT voltage of the device. As dashed line 408 follows relatively closely with the change in solid line 406, the temperature of the device as determined using the temperature sensing circuit was closely aligned with the temperature of the recipient model. Thus, determining a temperature of the device may allow for determining a temperature of a recipient as the temperature of the recipient may generally be substantially equal to the temperature of the device.

As with determining the temperature of the circuit allowing for determining the temperature of the device, there may be instances in which the device generates or receives heat and thus affects the temperature of the recipient and/or may not provide an accurate determination of the temperature of the recipient based solely on the temperature of the device. However, for similar reasons and/or using similar design choices, the temperature of the recipient may be determined. For example, the low-power architecture of the device may allow for heat generated by the device to be negligible. Additionally or alternatively, a processor may model, measure, and/or calculate heat generated and/or received by the device and incorporate such assessments into the determination of the temperature of the recipient based on the temperature of the device. Additionally or alternatively, the processor may wait a certain amount of time (e.g., based on how much heat may have been generated by the device, a predetermined amount of time, etc.) before determining the temperature of the recipient based on the temperature of the device. Additionally or alternatively, the processor may monitor the temperature of the device and/or determine the temperature of the device multiple times to detect when the temperature of the device remains within a threshold temperature difference for a threshold amount of time before determining the temperature of the recipient. Additionally or alternatively, the processor may determine whether the device is consuming less than a threshold amount of power, and based on such a determination, determine that the temperature of the recipient is substantially equal to the temperature of the device.

Determining the temperature of the recipient based on determining the temperature of the device using circuitry that is also used for providing medical benefit may provide various advantages. For example, the processor may provide an output based on the temperature of the recipient and/or the temperature of the device. The output may provide the determined temperature and/or an alert based on the determined temperature meeting a threshold temperature. For instance, if the recipient is a child and/or other medical patient, the device may allow for monitoring the temperature of the recipient and providing an alert if the recipient develops a fever or his or her temperature rises to some threshold for some reason.

Additionally or alternatively, optimal operation of the implantable device may be dependent on the temperature of the recipient. For example, the recipient's body temperature may affect the recipient's neural function. As a result, a specific amount of electrical stimulation provided by a cochlear implant may have different effects at different temperatures. Conversely, different amounts of electrical stimulation may be optimal at different temperatures for a cochlear implant to achieve a same effect. Being able to monitor the recipient's temperature may allow the implantable device (or another device that controls the implantable device) to account for such differences caused by temperature and adjust accordingly. To illustrate, based on the recipient's temperature, a sound processor may adjust parameters that control operation of a cochlear implant (e.g., a most comfortable stimulation level (e.g., an M level), a minimum level of stimulation at which the recipient may perceive the stimulation (e.g., a T level), a pulse width of one or more electrical stimulation pulses applied by the cochlear implant, and/or a duration of one or more stimulation pulses applied by the cochlear implant). As another example, the implantable device may change or adjust a program of operation based on the recipient's temperature, where the program may include a particular set of parameter values configured to optimize operation of the implantable device. For example, a gain of acoustic and/or electrical stimulation provided by an implantable device and/or a device (e.g., a device external to the recipient) in communication with an implantable device may be adjusted based on a temperature of the implantable device and/or recipient. Additionally or alternatively, being able to monitor the recipient's temperature may allow for testing to determine such differences and/or optimal adjustments for the implantable device.

Monitoring the temperature of the device may also be useful during operation of the device to ensure safety of the recipient. For example, the recipient may be harmed if the temperature of the device rises too high. Thus, the processor may monitor the temperature of the device during operations of the device that are likely to cause the device temperature to rise a threshold amount. For instance, the device may include a rechargeable battery. During charging of the rechargeable battery, the device may monitor the temperature of the device to ensure the temperature does not rise to or past a predetermined threshold. The processor may provide an alert if the threshold is met. Additionally or alternatively, the processor may provide a command to stop or pause the operation that is causing the rise in temperature. In this example, the processor may pause charging of the battery for a period of time or until the temperature drops a threshold amount.

As another example, an implantable pump configured to deliver insulin to a recipient may monitor temperature of the device and/or recipient and adjust a delivery of a substance in response to a change in the temperature. For example, an increase in temperature within a recipient may cause a corresponding increase in blood glucose level. Accordingly, in response to the increase in temperature, the implantable pump may preemptively deliver an increased amount of insulin to the recipient.

Any of the alerts, notifications, and/or actions described herein that may be performed in response to a detection of a temperature of an implantable device and/or recipient may be customized and/or prevented from occurring based on a particular recipient's needs and/or preferences. For example, a user may disable an alert, prevent an alert from being generated, customize contents of an alert, etc. As another example, an automatic action (e.g., gain adjustments and/or program modifications) may be prevented from being performed for a recipient.

The temperature-sensing architecture may also allow for monitoring temperature of the device during manufacture, initial testing, and/or initialization. For example, the processor may monitor the device temperature to ensure the device temperature does not reach a threshold temperature that may damage or otherwise affect components on the device. If such a threshold temperature is reached, the processor may provide an output so that the device may be replaced or repaired before being implanted in the recipient.

Figure 5:
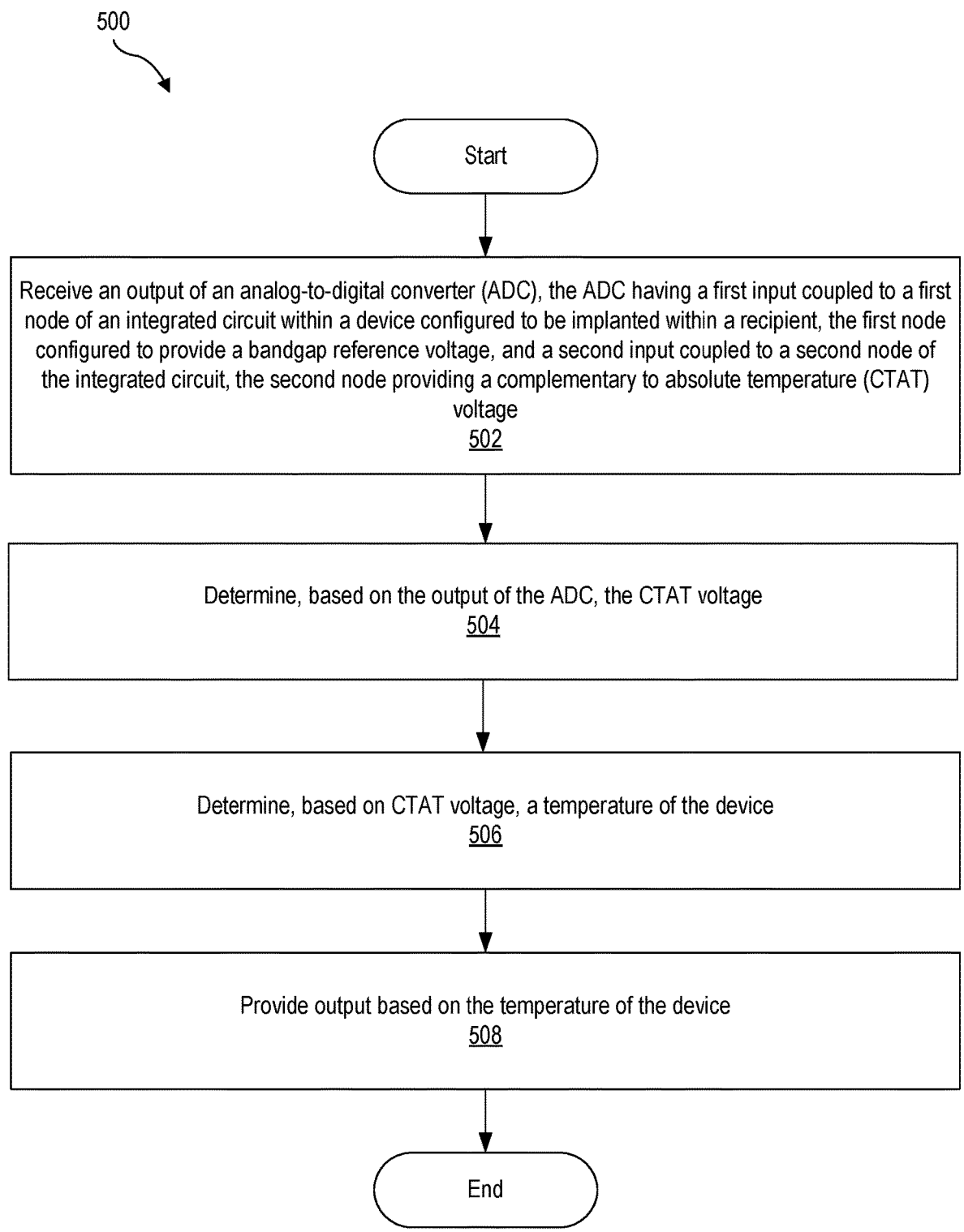
FIG. 5 illustrates an exemplary method according to principles described herein.

FIG. 5 illustrates an exemplary method 500 for sensing temperature with an implantable device. While FIG. 5 illustrates exemplary operations according to one embodiment, other embodiments may omit, add to, reorder, and/or modify any of the operations shown in FIG. 5.

In operation 502, a processor receives an output of an ADC, the ADC having a first input coupled to a first node of an integrated circuit within a device configured to be implanted within a recipient, the first node configured to provide a bandgap reference voltage, and a second input coupled to a second node of the integrated circuit, the second node providing a CTAT voltage. Operation 502 may be performed in any of the ways described herein.

In operation 504, the processor determines, based on the output of the ADC, the CTAT voltage. Operation 504 may be performed in any of the ways described herein.

In operation 506, the processor determines based on the CTAT voltage, a temperature of the device. Operation 506 may be performed in any of the ways described herein.

In operation 508, the processor provides an output based on the temperature of the device. Operation 508 may be performed in any of the ways described herein.

As mentioned, implantable device 102 may be implemented by a cochlear implant included in a cochlear implant system and processor 104 may be implemented by a sound processor included in the cochlear implant system. As such, an exemplary cochlear implant system will now be described.

Figure 6:
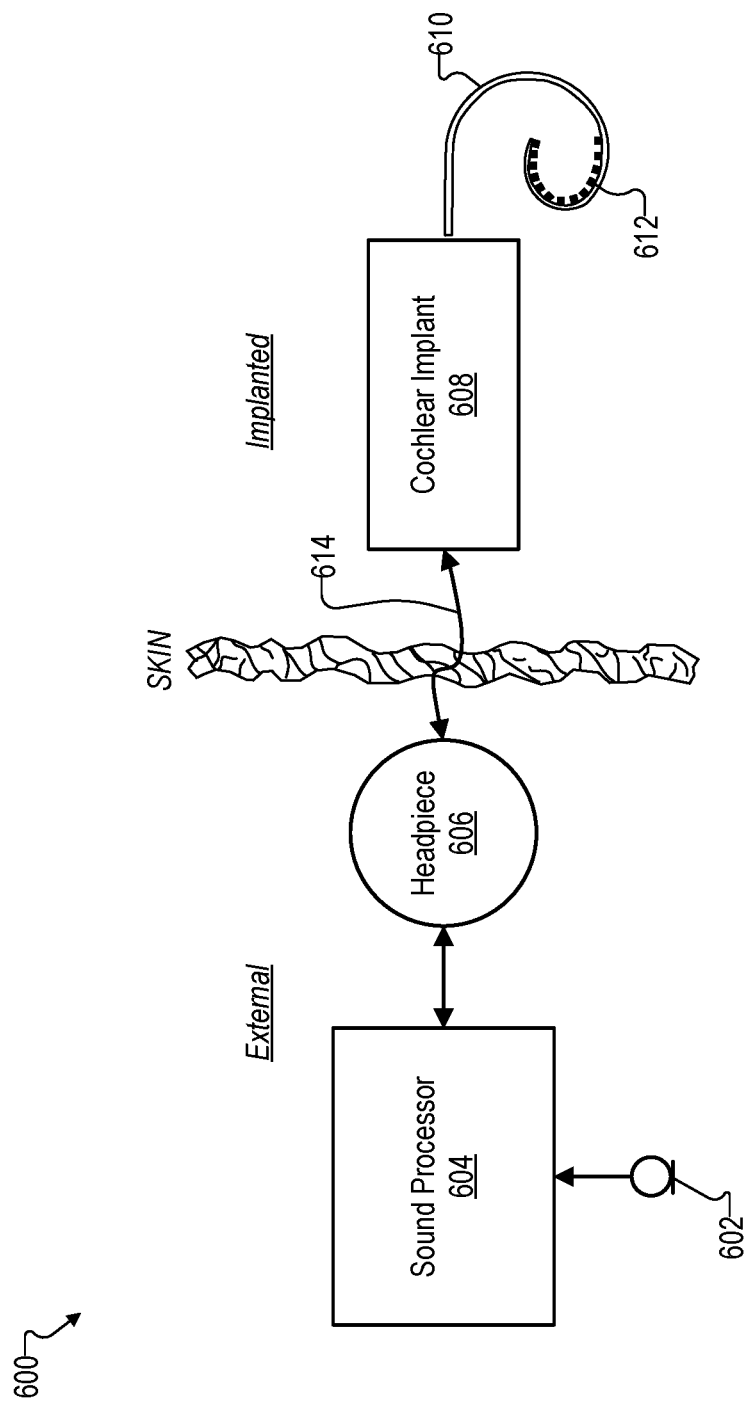
FIG. 6 illustrates an exemplary cochlear implant system according to principles described herein.

FIG. 6 illustrates an exemplary cochlear implant system 600. As shown, cochlear implant system 600 may include a microphone 602, a sound processor 604, a headpiece 606 having a coil disposed therein, a cochlear implant 608, and an electrode lead 610. Electrode lead 610 may include an array of electrodes 612 disposed on a distal portion of electrode lead 610 and that are configured to be inserted into a cochlea of a recipient to stimulate the cochlea when the distal portion of electrode lead 610 is inserted into the cochlea. One or more other electrodes (e.g., including a ground electrode, not explicitly shown) may also be disposed on other parts of electrode lead 610 (e.g., on a proximal portion of electrode lead 610) to, for example, provide a current return path for stimulation current generated by electrodes 612 and to remain external to the cochlea after electrode lead 610 is inserted into the cochlea. As shown, electrode lead 610 may be pre-curved so as to properly fit within the spiral shape of the cochlea. Additional or alternative components may be included within cochlear implant system 600 as may serve a particular implementation.

As shown, cochlear implant system 600 may include various components configured to be located external to a recipient including, but not limited to, microphone 602, sound processor 604, and headpiece 606. Cochlear implant system 600 may further include various components configured to be implanted within the recipient including, but not limited to, cochlear implant 608 and electrode lead 610.

Microphone 602 may be configured to detect audio signals presented to the user. Microphone 602 may be implemented in any suitable manner. For example, microphone 602 may include a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 604. Additionally or alternatively, microphone 602 may be implemented by one or more microphones disposed within headpiece 606, one or more microphones disposed within sound processor 604, one or more beam-forming microphones, and/or any other suitable microphone as may serve a particular implementation.

Sound processor 604 may be configured to direct cochlear implant 608 to generate and apply electrical stimulation (also referred to herein as "stimulation current") representative of one or more audio signals (e.g., one or more audio signals detected by microphone 602, input by way of an auxiliary audio input port, input by way of a clinician's programming interface (CPI) device, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 604 may process the one or more audio signals in accordance with a selected sound processing strategy or program to generate appropriate stimulation parameters for controlling cochlear implant 608. Sound processor 604 may be housed within any suitable housing (e.g., a behind-the-ear ("BTE") unit, a body worn device, headpiece 606, and/or any other sound processing unit as may serve a particular implementation). Sound processor 604 may be an implementation of processor 104.

In some examples, sound processor 604 may wirelessly transmit stimulation parameters (e.g., in the form of data words included in a forward telemetry sequence) and/or power signals to cochlear implant 608 by way of a wireless communication link 614 between headpiece 606 and cochlear implant 608 (e.g., a wireless link between a coil disposed within headpiece 606 and a coil physically coupled to cochlear implant 608). It will be understood that communication link 614 may include a bi-directional communication link and/or one or more dedicated uni-directional communication links.

Headpiece 606 may be communicatively coupled to sound processor 604 and may include an external antenna (e.g., a coil and/or one or more wireless communication components) configured to facilitate selective wireless coupling of sound processor 604 to cochlear implant 608. Headpiece 606 may additionally or alternatively be used to selectively and wirelessly couple any other external device to cochlear implant 608. To this end, headpiece 606 may be configured to be affixed to the recipient's head and positioned such that the external antenna housed within headpiece 606 is communicatively coupled to a corresponding implantable antenna (which may also be implemented by a coil and/or one or more wireless communication components) included within or otherwise associated with cochlear implant 608. In this manner, stimulation parameters and/or power signals may be wirelessly transmitted between sound processor 604 and cochlear implant 608 via communication link 614.

Cochlear implant 608 may include any suitable type of implantable stimulator. For example, cochlear implant 608 may be implemented by an implantable cochlear stimulator. Additionally or alternatively, cochlear implant 608 may include a brainstem implant and/or any other type of cochlear implant that may be implanted within a recipient and configured to apply stimulation to one or more stimulation sites located along an auditory pathway of a recipient.

In some examples, cochlear implant 608 may be configured to generate electrical stimulation representative of an audio signal processed by sound processor 604 (e.g., an audio signal detected by microphone 602) in accordance with one or more stimulation parameters transmitted thereto by sound processor 604. Cochlear implant 608 may be further configured to apply the electrical stimulation to one or more stimulation sites (e.g., one or more intracochlear regions) within the recipient via electrodes 612 disposed along electrode lead 610. In some examples, cochlear implant 608 may include a plurality of independent current sources each associated with a channel defined by one or more of electrodes 612. In this manner, different stimulation current levels may be applied to multiple stimulation sites simultaneously by way of multiple electrodes 612. Cochlear implant 608 may be an implementation of implantable device 102.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a device configured to be implanted within a recipient and comprising an integrated circuit comprising:
      a first node configured to provide a bandgap reference voltage, the first node coupled to a first input of an analog-to-digital converter (ADC), and
      a second node providing a complementary to absolute temperature (CTAT) voltage, the second node coupled to a second input of the ADC; and
   a processor communicatively coupled to an output of the ADC and configured to:
      determine, based on the output of the ADC, the CTAT voltage, and determine, based on the CTAT voltage, a temperature of the device, wherein the determining the temperature of the device comprises:
  determining a difference between the CTAT voltage and the bandgap reference voltage, and
  determining, based on the difference between the CTAT voltage and the bandgap reference voltage, and based on a known temperature response of the CTAT voltage, the temperature of the device.

2. The system of claim 1, wherein the processor is further configured to determine, based on the temperature of the device, a temperature of the recipient.

3. The system of claim 2, wherein the determining the temperature of the recipient comprises:
  determining the device is consuming less than a threshold amount of power; and
  determining, based on the device consuming less than the threshold amount of power, that the temperature of the recipient is substantially equal to the temperature of the device.

4. The system of claim 2, wherein the determining the temperature of the recipient comprises:
  determining the temperature of the device has remained within a threshold temperature difference for at least a threshold amount of time; and
  determining, based on the temperature of the device having remained within the threshold temperature difference for at least the threshold amount of time, that the temperature of the recipient is substantially equal to the temperature of the device.

5. The system of claim 2, wherein the processor is further configured to provide an output based on at least one of the temperature of the device and the temperature of the recipient.

6. The system of claim 5, wherein the output indicates at least one of the temperature of the device and the temperature of the recipient.

7. The system of claim 5, wherein the output comprises an alert based on at least one of the temperature of the device and the temperature of the recipient meeting a threshold temperature.

8. The system of claim 1, wherein the processor is housed within the device.

9. The system of claim 1, wherein the processor is external to the device and configured to be located external to the recipient.

10. The system of claim 1, wherein:
  the device comprises a cochlear implant configured to generate electrical stimulation based on the bandgap reference voltage; and
  the processor comprises a sound processor configured to control an operation of the cochlear implant.

11. The system of claim 10, wherein the sound processor is further configured to:
  adjust, based on the temperature of the device, a parameter that controls the electrical stimulation; and
  transmit the parameter to the cochlear implant.

12. A method comprising:
  receiving, by a processor, an output of an analog-to-digital converter (ADC), the ADC having
    a first input coupled to a first node of an integrated circuit within a device configured to be implanted within a recipient, the first node configured to provide a bandgap reference voltage, and
    a second input coupled to a second node of the integrated circuit, the second node providing a complementary to absolute temperature (CTAT) voltage;
  determining, by the processor, based on the output of the ADC, the CTAT voltage;
  determining, by the processor, based on the CTAT voltage, a temperature of the device, wherein the determining the temperature of the device comprises:
    determining a difference between the CTAT voltage and the bandgap reference voltage, and
    determining, based on the difference between the CTAT voltage and the bandgap reference voltage, and based on a known temperature response of the CTAT voltage, the temperature of the device; and
  providing, by the processor, an output based on the temperature of the device.

13. The method of claim 12, the method further comprising determining, by the processor, based on the temperature of the device, a temperature of the recipient.

14. The method of claim 13, wherein the determining the temperature of the recipient comprises at least one of:
  determining the device is consuming less than a threshold amount of power, and determining, based on the device consuming less than the threshold amount of power, that the temperature of the recipient is substantially equal to the temperature of the device; and
  determining the temperature of the device has remained within a threshold temperature difference for at least a threshold amount of time, and determining, based on the temperature of the device having remained within the threshold temperature difference for at least the threshold amount of time, that the temperature of the recipient is substantially equal to the temperature of the device.

* * * * *